United States Patent
Gianelli

(10) Patent No.: US 7,211,279 B1
(45) Date of Patent: May 1, 2007

(54) NUTRACEUTICAL METHOD AND ADDITIVE FOR IMPROVING HUMAN PHYSIOLOGY

(76) Inventor: Jason Gianelli, 49 Georgia St., East Northport, NY (US) 11731

( * ) Notice: Subject to any disclaimer, the term of this patent is extended or adjusted under 35 U.S.C. 154(b) by 0 days.

(21) Appl. No.: 11/297,048

(22) Filed: Dec. 8, 2005

(51) Int. Cl.
*A61K 36/28* (2006.01)
*A61K 36/00* (2006.01)

(52) U.S. Cl. ...................... 424/764; 424/725

(58) Field of Classification Search ............... None
See application file for complete search history.

(56) References Cited

U.S. PATENT DOCUMENTS

| | | | | |
|---|---|---|---|---|
| 5,614,224 | A * | 3/1997 | Womack | 424/646 |
| 5,895,652 | A * | 4/1999 | Giampapa | 424/195.17 |
| 6,488,957 | B1 * | 12/2002 | Koumarianos | 424/439 |
| 2003/0224071 | A1 * | 12/2003 | Murad | 424/728 |
| 2004/0096479 | A1 * | 5/2004 | Levine | 424/439 |

OTHER PUBLICATIONS

2001. Jack Challen. "How to avoid the diabetes epidemic". Let's Live.*

* cited by examiner

*Primary Examiner*—Christopher R. Tate
*Assistant Examiner*—Melenie McCormick
(74) *Attorney, Agent, or Firm*—Mitchell A. Stein; Stein Law, P.C.

(57) ABSTRACT

A method for creating a coffee drink that having the addition of a nutraceutical additive composition of milk thistle; chromium picolinate, and carnitine. Milk thistle is present from about 50 to 99.7 parts by weight of the total composition, and preferably 50 to 60 parts by weight. Chromium picolinate is present from about 0.01 to 0.23 parts by weight of the composition and preferably from 0.01 to 0.1 parts by weight. Carnitine is present from about 0 to 50 parts by weight of the total composition, and preferably 40 to 50 parts by weight. The coffee drink can be created by an admixture of the composition with ground beans, sprayed and/or coated on the bean prior to grinding, or added to a brewed much the same as one would add sugar or other known flavor additives. The instant composition does not subtract from the flavor and improves human physiology by assisting in weight loss, body cleansing, weight loss, fat burning, and sugar regulation.

9 Claims, 2 Drawing Sheets

NUTRACEUTICAL METHOD AND ADDITIVE FOR IMPROVING HUMAN PHYSIOLOGY

FIELD OF THE INVENTION

The present invention involves a nutraceutical composition designed for improving human physiology and in particular a unique synergistic combination of components that, when added to coffee, improve immunological response, body cleansing, weight loss, burning of body fat, and sugar control.

BACKGROUND OF THE INVENTION

The instant invention relates to a flavorless synergistic nutraceutical composition which can be added to coffee in its many forms to promote health and prevent disease and/or illnesses. The nutraceutical composition described in the instant invention can be added by mixing the composition with a desired anhydrous coffee before water is added, or by adding the composition directly to the coffee after it is hydrated.

Nutraceuticals, also known as phytochemicals, are natural, bioactive chemical compounds that provide numerous physiological benefits, including, inter alia, disease prevention and health promotion. Nutraceudicals are used to achieve both long-term and short-term health objectives. There are a huge, varied and almost unlimitless variety of nutraceuticals. This application, having reviewed the thousands available, demonstrates a synergistic interplay among the three selected, which are critical, at the ranges selected.

Nutraceuticals supplement the diet. Nutraceuticals can be either purified or concentrated by using bioengineering methods. Nutraceuticals can also be enhanced through genetic methods, which contain elevated levels of natural substances. Nutraceuticals are a low cost nutritional supplement which the consumer can ostensibly use to manage their own health care, increasing or decreasing the use (or frequency of use) thereof as the consumer sees fit, based either on their own perceived needs or on the advice of a medical doctor. Unfortunately, however, most information is unreliable and scant, and the individual is frequently unable to make proper or rational decisions to improve his or her health. The instant invention "takes the guess work out of it."

Various types of nutraceuticals include isolated nutrients, including one or more dietary supplements or herbal products. Nutraceuticals contain at least one of the following dietary ingredients: a vitamin, a mineral, an herb or other botanical, an amino acid, a metabolite, constituent, extract, or combination of these ingredients. Common examples of nutraceuticals include beta-carotene (used to prevent cardiac arrest), ephedra (used to aid in weight loss), ginko biloba (used as a circulatory stimulant), goldenseal (used in the prevention and/or treatment of infectious diseases), valerian (used as a sedative and anxiolytic), ginseng (used for stress relief and restoration of homeostasis), and echinacea (used for prophylaxis and treatment of viral, bacterial and fungal infections).

As demonstrated above, a wide variety of nutraceuticals have previously been implemented in the treatment of various physiological and pathological conditions. For example, Konishi, U.S. Pat. No. 6,932,990 discloses a carbohydrate absorption inhibitor derived from the nutraceudical evening primrose seed. McPeak, U.S. Pat. No. 6,902,739 discloses formulations for treating an inflammatory disease or reducing an inflammatory reaction comprising via a fortified formulation comprising rice bran derivative and a fortification agent. Shashoua, U.S. Pat. No. 6,890,896 discloses a composition using various nutraceuticals to counteract harmful oxidative effects of reactive oxygen species and other free radicals. Giori, U.S. Pat. No. 6,881,426 discloses an extract of the nutraceutical echinacea to strengthen immune defenses of the lymphatic system. Mousa, U.S. Pat. No. 6,866,864 discloses a garlic-derived compound for the prevention and treatment of vascular-related disorders. Hong, U.S. Pat. No. 6,827,950 discloses a composition comprising extracts of the nutraceutical aralia to preven cataract, delay the development of cataract, and treat cataract. Nair, U.S. Pat. No. 6,818,324 discloses an extract of the nutraceutical anthocyanin for pain relief and anti-inflammation. Holub, U.S. Pat. No. 6,784,159 discloses the use of the nutraceutical soyasaponin B. sub. b for the treatment of polycystic kidney disease. Butters, U.S. Pat. No. 6,761,913 discloses an extract of celery seed for treatment and prevention of acute and chronic pain, inflammation and gastrointestinal irritation. Heeg, U.S. Pat. No. 6,733,798 discloses cranberry seed oil for the treatment of burned tissue. Garrity, U.S. Pat. No. 6,703,333 discloses a composition including the nutraceutical mangosteen for improving general health and wellness. Nair, U.S. Pat. No. 6,623,743 describes a nutraceutical composition comprising anthocyanins, bioflavonoids, phenolics or mixtures thereof from cherries for inhibiting oxidation. Cartwright, U.S. Pat. No. 6,585,998 discloses a nutraceutical composition including a tripeptoid component, a flavonoid component, guanidine hydrochloride, .alpha.-lipoic acid, an amino acid component, a brazilin component, catalase, and, optionally, vitamin E ans selenium to maintain normal blood sugar levels and normal levels of non-enzymatic protein glycosylation. Henderson, U.S. Pat. No. 6,492,349 discloses a composition including the nutraceuticals glucosamine and chondroitin sulfate for the treatment and repair of connective tissue.

Heretofore, unknown in the art is the specific, synergistic combination that is disclosed and claimed herein. To the inventor's knowledge, there has been no composition of nutraceuticals that can be added to coffee without undergoing a mechanical process (most suited to large bottlers in the industry), or altering the flavor of the beverage, or losing any potential beneficial effects. For example, Nickolas, U.S. Pat. No. 6,855,358 discloses a process for the addition of a nutraceutical to a beverage by treating a beverage with a sterilizing agent, filling a container with the beverage, and finally adding an amount of a nutraceutical and sealing said container. It has now been discovered that admixtures of specific flavorless nutraceuticals have broad physiological effects and can easily be added to coffee for consumption.

It is thus an object of the instant invention to provide a composition that can be either admixed with ground coffee, applied to unground coffee beans, or added directly to a brewed cup of coffee that adds no negative flavor and improves human physiology without any known adverse side effects.

SUMMARY OF THE INVENTION

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

The foregoing objects and other objects of the invention are achieved through a method for creating a coffee drink that having the addition of a nutraceutical additive composition of milk thistle; chromium picolinate, and carnitine. Milk thistle is present from about 50 to 99.7 parts by weight of the total composition, and preferably 50 to 60 parts by weight. Chromium picolinate is present from about 0.01 to 0.23 parts by weight of the composition and preferably from 0.01 to 0.1 parts by weight. Carnitine is present from about 0 to 50 parts by weight of the total composition, and preferably 40 to 50 parts by weight. The coffee drink can be created by an admixture of the composition with ground beans, sprayed and/or coated on the bean prior to grinding, or added to a brewed much the same as one would add sugar or other known flavor additives.

The instant composition does not subtract from the flavor and improves human physiology by assisting in weight loss, body cleansing, weight loss, fat burning, and sugar regulation.

The foregoing objects and other objects of the invention are achieved through admixing various nutraceuticals to create a composition which can be added to coffee in order to promote health and prevent disease and/or illnesses. The composition of the invention consists of the following ingredients: milk thistle, chromium picolinate, and carnitine.

The composition of the instant invention can be added to coffee, hot or cold, without altering the flavor. It is a synergistic composition, the components are critical and the amounts are critical in order to provide the benefits discussed hereinabove and to prevent any deterioration in the flavor of the coffee. These components and the quantities are the result of numerous experiments and data accumulation in concluding efficacy.

Consumption of the composition will provide numerous physiological benefits including, but not limited to: detoxification of the body, the burning of body fat, and control of sugar (insulin-styled) levels. Milk Thistle acts to protect and regenerate the liver resulting from damage caused by liver diseases such as Cirrhosis (hardening of the Liver), Jaundice and Hepatitis, (inflammation of the Liver), and Cholangitis (inflammation of bile ducts resulting in decreased bile flow). Milk thistle acts not only to protect each cell of the liver from incoming toxins, but simultaneously encourages the liver to cleanse itself of damaging substances (toxins).

The nutraceudical chromium picolinate functions to increase the efficiency of insulin to optimal levels. This nutraceudical is a combination of the element chromium and picolinic acid. Chromium is a naturally-occurring mineral, trace amounts of which are found in the food in which we consume everyday. Use of chromium has been found to improve glucose tolerance, serum lipid concentrations, including high-density lipoprotein cholesterol, insulin and insulin binding. Chromium has been found to enable insulin to function properly and helps the body metablize carbohydrates and fats. The main function of insulin is to transport glucose to the various cells of the body so as to provide the energy that allows cells to perform their various function(s).

Chromium has also has been found to improve the ability of people suffering from glucose intolerance to remove excess sugar from their blood after eating. Finally, due to its ability to breakdown fat, chromium has been found to be useful for reducing cholesterol in the blood.

The picolinic acid in chromium picolinate has been found as a metabolite of amino acids, produced from tryptophan in the liver, kidney and pancreas, and also known to be a physiological carrier for zinc, copper and chromium ions during their transport from the small intestine to the blood.

Carnitine, an essential nutrient, is a derivative of amino acid, lysine. Carnitine is synthesized primarily in the liver and the kidneys. Carnitine plays functions improving energetics (the production of energy (ATP)) by transporting long-chain fatty acids (acyl-CoA) across the mitochondrial membrane and into the mitochondrion for metabolism (beta oxidation) and then removing unwanted compounds therefrom. As such carnitine deficiencies result in reduced muscle response, both voluntary and involuntary (autonomic).

Thus, after detailed study and analysis the instant invention combines these three critical ingredients and has been discovered to improve the human condition without disrupting the flavor of coffee. Coffee, a key beverage, with this composition has been shown to improve the human condition in all the ways discussed above.

The composition of the instant invention is added to coffee before or after hydration, without altering the taste of coffee. To facilitate use and portability, the composition can also be packaged in packets in which an amount of the composition is contained which corresponds to the amount used for a specific volume of beverage (a 12 ounce serving, for example). Said packet will act to sterilize the composition of the instant invention without a substantial loss of activity, or change in the structure, of the nutraceuticals contained in said composition.

Other features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements through the several views.

DETAILED DESCRIPTION OF THE PREFERRED EMBODIMENTS

Figure 1:
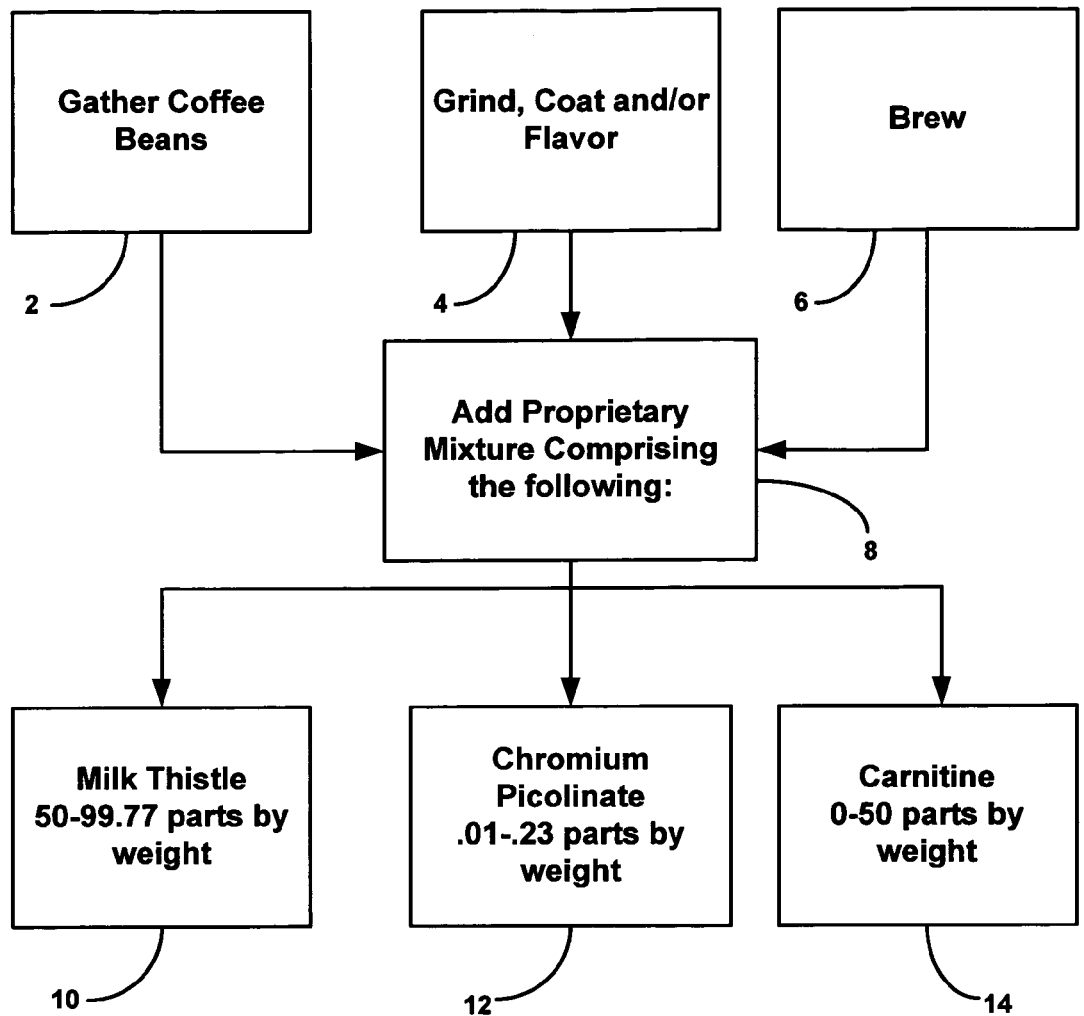
FIG. 1 is an overview of the instant invention showing the preferred embodiments, method and composition.

In accordance with the subject invention, FIG. 1 shows an overall view of the various mechanisms of enhancing coffee, as well as the proprietary composition. In particular, coffee is a critical ingredient in the invention. As such, coffee beans are gathered at step 2, it being understood that gathering can be of beans of any flavor and any geographical location, depending on the desire of the person who is consuming the beverage.

Under one variation of the invention, coffee beans are gathered at 2, and the proprietary mixture added at step 8, it being understood that the beans are generally either coated or sprayed with the admixture of composition at step 4 or ground before use. In the latter (grinding), the admixture is mixed with the ground coffee before brewing at step 6.

The proprietary mixture is added at step 8. As shown in FIG. 1 it has been determined that three key ingredients are critical, in ranges indicated at 10, 12 and 14, in order for the coffee beverage to achieve the efficacy sought. In particular, at step 10, milk thistle is added at 50–99.77 parts by weight, it being understood that weight is weight of the total admixture of the three components, irrespective of the quantity of coffee. Likewise, at step 12, chromium picolinate is added at 0.01 to 0.23 parts by weight, and at step 14, carnitine is added at between 0 and 50 party by weight.

Figure 2:
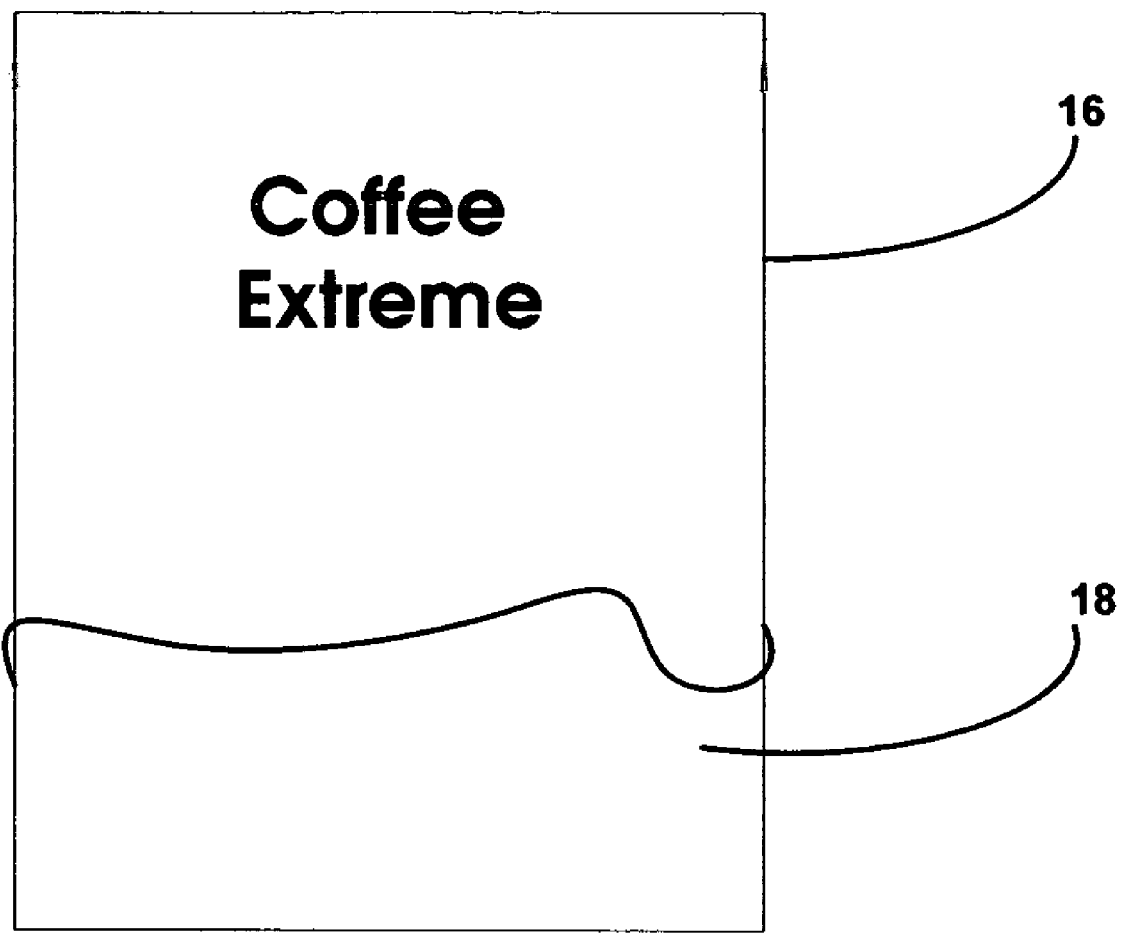
FIG. 2 is a package design view for containing the composition for addition to coffee after brewing.

FIG. 2 shows a package 16 that can be utilized in accordance with the subject invention containing contents 18 at the same quantities as those shown in 10, 12 and 14. It is generally recognized that coffee drinkers add many substances to coffee, including, for example, sugar, milk, cream, sugar substitutes and the like. It has been discovered herein that all can be added without interference with contents 18, provided the contents conform with the quantities indicated in 10, 12 and 14. Thus, the consumer can tear open package 16 in normal manner (it being comprised of generally accepted material), the contents added to coffee, and any other contents to add flavor also added. One of ordinary skill in the art will appreciate that contents 10, 12 and 14 shown as 18 in FIG. 2 will not add any significant flavor to the coffee, and hence any flavor enhancement is left to the consumer, while the benefits derived from the critical composition are achieved.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

I claim:

1. A method for creating a nutraceutical-enriched coffee drink comprising the addition of a flavorless nutraceutical additive composition to a coffee drink preparation, wherein the composition comprises:
    (a) milk thistle;
    (b) chromium picolinate, and
    (c) carnitine.

2. The method of claim 1, wherein component (a) of the composition of claim 1 comprises from about 50 to 99.7 parts by weight of the total composition.

3. The method of claim 1, wherein component (b) of the composition of claim 1 comprises from about 0.01 to 0.23 parts by weight of the composition.

4. The method of claim 1, wherein component (c) of the composition of claim 1 comprises from about 40 to 50 parts by weight of the total composition.

5. The method of claim 1, wherein the coffee drink preparation is created by admixture of the composition to ground coffee beans.

6. The method of claim 1, wherein the coffee drink is created by spraying or coating coffee beans prior to grinding with the composition.

7. The method of claim 1, wherein the coffee drink is first brewed, and then the composition is added thereto.

8. A flavorless composition for addition to coffee, comprising;
    (a) milk thistle in an amount ranging from 50 to 60 parts by weight;
    (b) chromium picolinate in an amount ranging from 0.01 to 1 parts by weight; and
    (c) carnitine in an amount ranging from 40 to 50 parts by weight.

9. The method of claim 1 wherein:
    (a) component (a) of the composition of claim 1 comprises 50 to 60 parts by weight;
    (b) component (b) of the composition of claim 1 comprises 0.01 to 0.1 parts by weight; and
    (c) component (c) of the composition of claim 1 comprises 40 to 50 parts by weight.

* * * * *